(12) United States Patent     (10) Patent No.:   US 12,678,027 B2

Simoff     (45) Date of Patent:     Jul. 14, 2026

| | | | | |
|---|---|---|---|---|
| (54) | BRONCHOSCOPY STAND | | | |
| | | 2,519,711 A * | 8/1950 | Sprechmann ......... A47F 7/0064 |
| (71) | Applicant: Michael J. Simoff, Northville, MI (US) | | | D7/602 |
| | | 2,629,498 A * | 2/1953 | Marasigan .............. A47J 47/16 |
| (72) | Inventor: Michael J. Simoff, Northville, MI (US) | | | D7/602 |
| | | 2,682,956 A * | 7/1954 | Pike ...................... A47F 5/0876 |
| (73) | Assignee: Michael J. Simoff, Northville, MI (US) | | | 211/85.15 |
| | | 2,689,703 A * | 9/1954 | Petzke ...................... A47F 7/00 |
| (*) | Notice: Subject to any disclaimer, the term of this patent is extended or adjusted under 35 U.S.C. 154(b) by 477 days. | | | 211/41.7 |
| | | 2,934,210 A * | 4/1960 | Jordan .................... A47J 47/20 |
| | | | | D6/678.4 |
| | | 3,168,329 A * | 2/1965 | Goldschmidt ............ B62B 3/12 |
| | | | | 211/195 |
| (21) | Appl. No.: 18/184,039 | 3,490,726 A * | 1/1970 | Mills ........................ A01K 5/01 |
| | | | | 248/312.1 |
| | | D216,690 S * | 3/1970 | Robak ............................ D7/704 |
| (22) | Filed: Mar. 15, 2023 | 3,532,225 A * | 10/1970 | Reed ........................ A47F 5/13 |
| | | | | 211/69.9 |
| (65) | Prior Publication Data | 3,858,835 A * | 1/1975 | Baren ........................ B01L 9/00 |
| | US 2023/0309799 A1    Oct. 5, 2023 | | | 211/74 |
| | | 4,730,799 A * | 3/1988 | Foss ........................ B25H 3/006 |
| | Related U.S. Application Data | | | 248/51 |
| (60) | Provisional application No. 63/324,717, filed on Mar. 29, 2022. | 4,819,899 A * | 4/1989 | Weil .......................... A47F 5/01 |
| | | | | 248/97 |

(Continued)

(51) Int. Cl.
*A61B 1/00*        (2006.01)

(52) U.S. Cl.
CPC ................................. *A61B 1/00147* (2013.01)

(58) Field of Classification Search
CPC ........ A61B 1/00147; A47B 55/02; A47F 5/01
USPC ....... 211/85.13, 181.1, 41.7, 41.11, 119.001, 211/125, 85.15; 248/153, 175, 312.1, 248/117.2, 117.3, 117.5
See application file for complete search history.

(56) References Cited

U.S. PATENT DOCUMENTS 1,371,253 A * 3/1921 Lynch ...................... A47L 19/04
                                                 220/572
D100,443 S * 7/1936 Sherrick ...................... D6/678.4

*Primary Examiner* — Jonathan Liu

(74) *Attorney, Agent, or Firm* — Quinn IP Law

(57)             ABSTRACT

Disclosed herein is a bronchoscopy stand usable for holding and supporting a bronchoscope. The bronchoscopy stand includes a base plate and a first tower extending vertically from a first edge of the base plate. A second tower extends vertically from the same edge of the base plate as the first tower. The first tower and the second tower are substantially parallel. A first receptacle groove is formed at an opposite end of the first tower from the base plate and a second receptacle groove is formed at an opposite end of the second tower from the base plate. A method for supporting a bronchoscope on scope stand is also provided.

19 Claims, 2 Drawing Sheets

(56)                References Cited

U.S. PATENT DOCUMENTS

| | | | | |
|---|---|---|---|---|
| 4,840,336 A * | 6/1989 | Stroh | B65B 67/1227 | |
| | | | D34/5 | |
| 5,031,783 A * | 7/1991 | Goudreau | A47F 5/083 | |
| | | | 248/222.51 | |
| 5,588,543 A * | 12/1996 | Finger | A47F 5/083 | |
| | | | 211/90.01 | |
| 5,740,928 A * | 4/1998 | Dale | B67D 3/0083 | |
| | | | 248/153 | |
| 5,743,417 A * | 4/1998 | Mathis | D06F 81/00 | |
| | | | 36/106 | |
| 5,826,731 A * | 10/1998 | Dardashti | A47B 73/002 | |
| | | | 211/74 | |
| 5,833,080 A * | 11/1998 | Donne | A47F 7/0064 | |
| | | | 248/175 | |
| 6,173,845 B1 * | 1/2001 | Higgins | A47F 7/28 | |
| | | | 211/74 | |
| 6,299,003 B1 * | 10/2001 | Osorio | A47L 15/505 | |
| | | | 211/181.1 | |
| 6,454,223 B1 * | 9/2002 | Rosky | B65B 67/1227 | |
| | | | 248/100 | |
| 6,564,950 B1 * | 5/2003 | Holm | A47B 55/02 | |
| | | | 248/905 | |
| 7,469,792 B1 * | 12/2008 | Lin | A47B 73/004 | |
| | | | 211/74 | |
| 7,611,019 B2 * | 11/2009 | Alvarado | A47F 13/085 | |
| | | | 211/85.15 | |
| 7,793,793 B1 * | 9/2010 | Sykes | A47F 5/13 | |
| | | | 211/85.2 | |
| D636,616 S * | 4/2011 | Clark | D6/683.1 | |
| 7,959,020 B2 * | 6/2011 | Rosen | D06F 79/02 | |
| | | | 248/302 | |
| 8,109,018 B2 * | 2/2012 | Maurer | D06F 79/02 | |
| | | | 38/142 | |
| 8,464,879 B2 * | 6/2013 | Black, Jr. | A47F 7/0014 | |
| | | | 211/195 | |
| 8,931,649 B2 * | 1/2015 | Chen | A47F 5/13 | |
| | | | 211/181.1 | |
| 9,949,564 B1 * | 4/2018 | Swisher | A01K 97/22 | |
| 11,780,630 B2 * | 10/2023 | Sill | B65D 33/001 | |
| | | | 53/459 | |
| D1,092,161 S * | 9/2025 | Kasza | D7/701 | |
| 2003/0000905 A1 * | 1/2003 | Zidek | A47F 5/01 | |
| | | | 211/90.03 | |
| 2003/0024891 A1 * | 2/2003 | Diamond | A61B 50/24 | |
| | | | 211/85.13 | |
| 2003/0173313 A1 * | 9/2003 | Morgan | A47F 5/01 | |
| | | | 211/184 | |
| 2005/0077256 A1 * | 4/2005 | Hassett | A47B 43/02 | |
| | | | 211/175 | |
| 2006/0102573 A1 * | 5/2006 | Alvarado | A47G 29/00 | |
| | | | 211/85.15 | |
| 2006/0102809 A1 * | 5/2006 | Broeders | B65F 1/1415 | |
| | | | 248/302 | |
| 2006/0289367 A1 * | 12/2006 | Cossey | A45D 44/06 | |
| | | | 211/13.1 | |
| 2007/0186515 A1 * | 8/2007 | Ruetten | G07G 1/0072 | |
| | | | 211/85.15 | |
| 2023/0309799 A1 * | 10/2023 | Simoff | A61B 1/00147 | |
| | | | 600/102 | |

* cited by examiner

BRONCHOSCOPY STAND

CROSS-REFERENCE TO RELATED APPLICATIONS

This application claims the benefit of U.S. Provisional Application No. 63/324,717, filed 29 Mar. 2022, which is hereby incorporated by reference in its entirety.

INTRODUCTION

This disclosure generally relates to stands usable with flexible or rigid bronchoscopes or endoscopes.

SUMMARY

A bronchoscopy stand usable for holding and supporting a bronchoscope is provided. The bronchoscopy stand includes a base plate and a first tower extending vertically from an edge or first edge of the base plate. A second tower extends vertically from the same edge of the base plate as the first tower. The first tower and the second tower are substantially parallel.

A first receptacle groove is formed at an opposite end of the first tower from the base plate and a second receptacle groove is formed at an opposite end of the second tower from the base plate. In some configurations, the first receptacle groove is substantially V-shaped and the second receptacle groove is substantially V-shaped.

In many configurations of the bronchoscopy stand at least two cross bars extend between, and are attached to, the first tower and the second tower. A third tower may extend vertically from the same edge of the base plate as the first tower and the second tower, and the third tower may intersect the uppermost of the cross bars.

For example, the base plate of the bronchoscopy stand may be substantially square. Additionally, a height of the first tower and the second tower may be at least twice the width of the base plate. A method for supporting a bronchoscope on scope stand is also provided.

The above features and advantages, and other features and advantages, of the present disclosure are readily apparent from the following detailed description of some of the best modes and other embodiments for carrying out the disclosure, which is defined solely by the appended claims, when taken in connection with the accompanying drawings.

DETAILED DESCRIPTION

Figure 2:
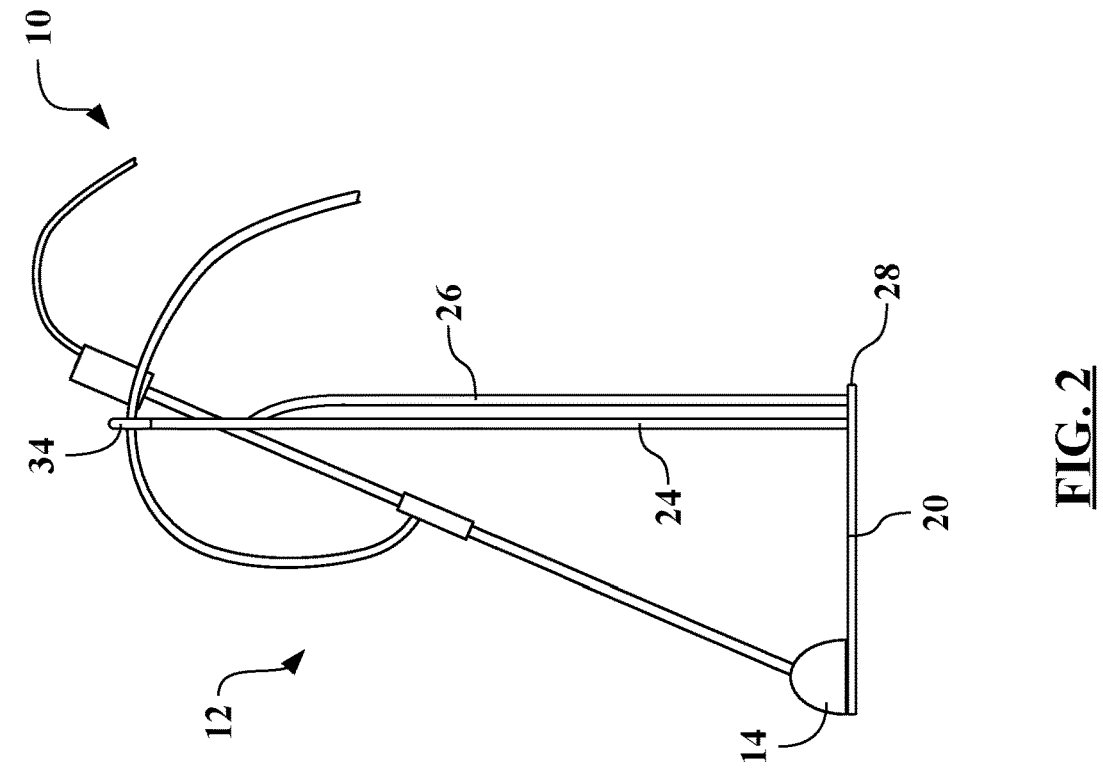
FIG. 2 schematically illustrates a side view of the bronchoscopy stand.

Referring to the drawings, like reference numbers correspond to like or similar components wherever possible throughout the several figures. All figures may be referred to in any section of the specification, without regard to numerical order.

Figure 1:
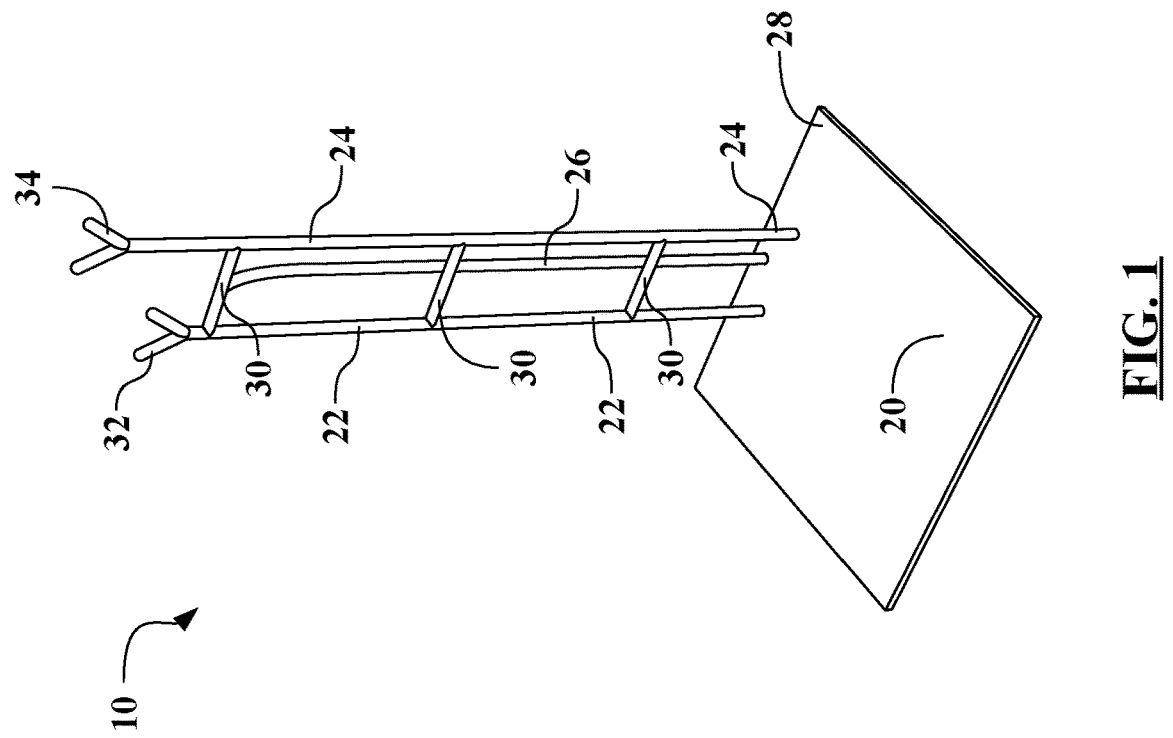
FIG. 1 schematically illustrates an isometric view of a bronchoscopy stand.
Figure 4:
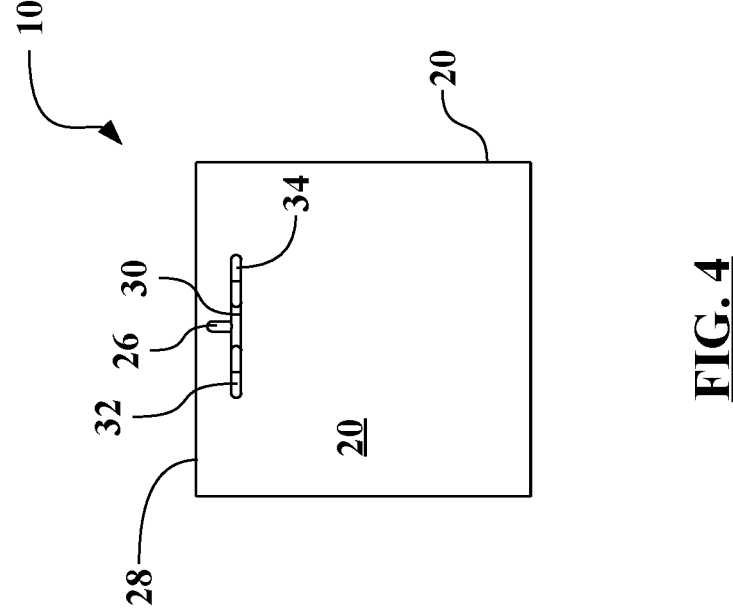
FIG. 4 schematically illustrates a top view of the bronchoscopy stand.
Figure 3:
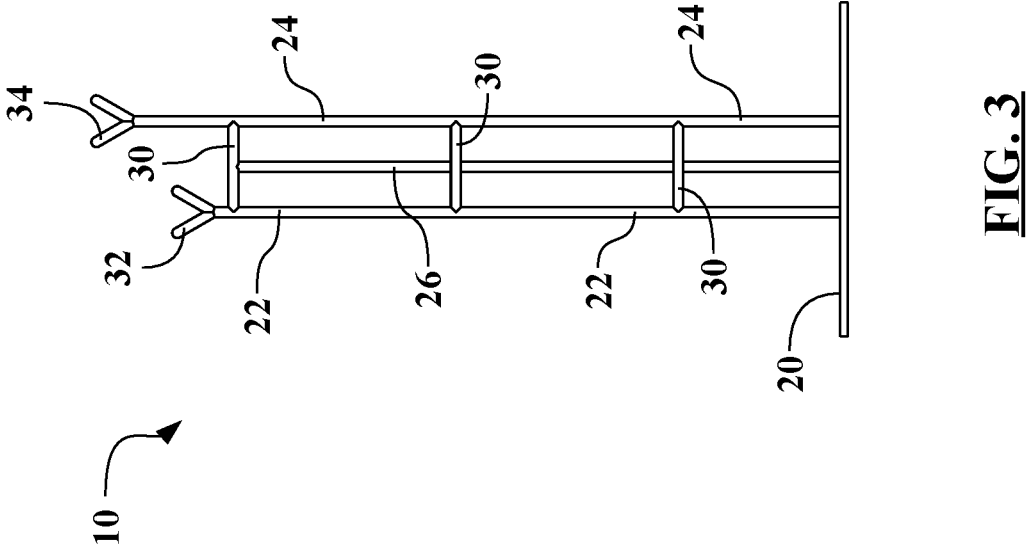
FIG. 3 schematically illustrates a front view of the bronchoscopy stand.

As schematically illustrated in FIGS. 1-4, there are various views of a stand 10 that may be used with an endoscope or bronchoscope 12, which is illustrated highly schematically in FIG. 2. FIG. 1 shows an isometric view of a stand 10; FIG. 2 shows a side view of the stand 10; FIG. 3 shows a front view of the stand 10; and FIG. 4 shows a top view of the bronchoscopy stand.

The stand 10 may be used with either a flexible bronchoscope 12 or a rigid bronchoscope 12, but is particularly useful with rigid bronchoscopes 12. The rigid bronchoscope 12 shown in FIG. 2 is illustrated as placed into a warming device, scope warmer, or simply warmer 14 that keeps a camera (not separately shown or numbered) warm to prevent subsequent fogging of a lens of the camera. The camera is located on a tip of the bronchoscope 12 and rests within the warmer 14.

While the present disclosure may be illustrated or described with respect to particular industries or applications, those skilled in the art will recognize the broader applicability of the products, methods, and techniques, described herein. For example, similar structures, methods, or combinations thereof, may be used in other industries or for medical procedures other than those described herein. The order of any method steps described herein is not limiting.

Those having ordinary skill in the art will also recognize that terms such as "above," "below," "upward," "downward," et cetera, are used descriptively of the figures, and do not represent limitations on the scope of the appended claims. Any numerical designations, such as "first" or "second" are illustrative only and are not intended to limit the scope of the claims in any way.

When used herein, the term "substantially" refers to relationships that are ideally perfect or complete, but where manufacturing realities prevent absolute perfection. Therefore, substantially denotes typical variance from perfection in the relevant art. For example, if height A is substantially equal to height B, it may be preferred that the two heights are 100.0% equivalent, but manufacturing realities likely result in the distances varying from such perfection. Skilled artisans would recognize the amount of acceptable variance in the specific industry. For example, and without limitation, coverages, areas, or distances may generally be within 10% of perfection for substantial equivalence. Similarly, relative alignments, such as parallel or perpendicular, may generally be within 5%.

Features shown in one figure may be combined with, substituted for, or modified by, features shown in any of the figures. Unless stated otherwise, no features, elements, or limitations are mutually exclusive of any other features, elements, or limitations. Any specific configurations shown in the figures are illustrative only and the specific configurations shown are not limiting.

The stand 10 may be formed from many different materials, only some examples of which are given here, and skilled artisans will recognize additional materials. Stainless steel is a likely material for the stand 10, as it generally prevents stains and/or rust and is a common material for medical environments. Other metals may also be used, including aluminum or alloys thereof, and other types of steel or alloys thereof, in addition to coated or plated metals. Additionally, numerous plastics may be used to form or construct the stand 10, as will be recognized by skilled artisans.

The stand 10 has several components to assist in holding up the bronchoscope 12 and making it easily accessible and useful in different environments, including operating rooms. As viewed in FIGS. 1-4, the stand 10 has a base plate 20. In the configuration shown, the base plate 20 is substantially square, but other shapes, including, without limitation, rectangles or ovals may also be used for the base plate 20.

A first tower 22 extends vertically from one edge, which may be referred to as a first edge 28, of the base plate 20 and a second tower 24 extending vertically from the same edge of the base plate 20 as the first tower 22. In the configuration shown, the first tower 22 and the second tower 24 are substantially parallel.

The bronchoscope 12 generally includes, at least, a suction device and the camera, which may be part of a Hopkins telescope that includes light and visualization capabilities. The Hopkins telescope is schematically illustrated in the figures but is not separately numbered. The bronchoscope 12 is often, but not necessarily, made of stainless steel and is hollow. Additionally, and without limitation, the hollow portions of the bronchoscope 12 may be configurated to allow passage of the telescope and/or a separate light source, suction catheter, balloons, laser fibers, forceps, stents, and other components that will be recognizable to skilled artisans. The bronchoscope 12 likely includes suction tubing and camera wires extending from upper portions thereof, as schematically illustrated in FIG. 2.

To support and retain the bronchoscope 12 in an upright position, a first receptacle groove 32 is formed at an opposite end of the first tower 22 from the base plate 20 and a second receptacle groove 34 is formed at an opposite end of the second tower 24 from the base plate 20. Either of the first receptacle groove 32 or the second receptacle groove 34 may be used to support the bronchoscope 12.

Additionally, the first receptacle groove 32 or the second receptacle groove 34, particularly whichever groove is not supporting the bronchoscope 12, may be used to support or hold the wires, hoses, or tubes attached to the bronchoscope 12—this is schematically illustrated in FIG. 2, where example tubing passes through the second receptacle groove 34.

In the example configuration shown in the figures, the first receptacle groove 32 and the second receptacle groove 34 are substantially V-shaped. This shape provides a solid mechanism for holding either the bronchoscope 12, wires and tubes attached thereto, or both. Note that other shapes may be used for the first receptacle groove 32 and the second receptacle groove 34, including, without limitation, U or C shapes.

A third tower 26 also extends vertically from the same edge of the base plate 20 as the first tower 22 and the second tower 24. The third tower 26 is clustered with the first tower 22 and the second tower 24 on the first edge 28 of the base plate 20. At least two cross bars 30 extend between, and are attached to, the first tower 22 and the second tower 24. In the configuration shown, and without limitation, there are three cross bars 30, which may be substantially perpendicular to the first tower 22 and the second tower 24. The third tower 26 intersects and is joined to the uppermost cross bar 30, as best viewed in FIG. 1, such that the third tower 26 is slightly curved at the top, which is not a limiting configuration.

The third tower 26 is also located at the first edge 28 of the base plate 20, as viewed in the figures. Note that the first edge 28 is a general area and is not limiting.

As schematically illustrated, the first tower 22 and the second tower 24 are relatively tall, such that different lengths of bronchoscopes 12 may be held by the stand 10. In one exemplary configuration, and without limitation, the height of both the first tower 22 and the second tower 24 are at least twice the width of the base plate 20. Where the base plate 20 is not substantially square, it may be that the height of the first tower 22 and the second tower 24 will at least twice the length of the base plate 20.

There are generally two types, or lengths, of bronchoscopes 12, which are described here without limitation and are for example only. A tracheal bronchoscope 12 may be approximately 33 centimeters in length and a bronchial bronchoscope 12 may be approximately 43 centimeters in length. The stand 10 includes the different heights of the first tower 22 and the second tower 24 to easily accommodate either of the example lengths of the bronchoscope 12 used.

Without the stand 10, management of the bronchoscope 12 occurs by simply laying the bronchoscope 12 on a surgical table with the suction tubing and camera wires splayed out. However, this alternative often results in tangling of the tubes or wires and does not provide support for the bronchoscope 12, which may make it difficult to use the bronchoscope 12 for a surgical procedure.

Additionally, the bronchoscope 12 can easily be knocked off the table by movement, or catching, of the camera wires, hoses, or tubes. With the bronchoscope 12 laying across the surgical table, there is limited workable space on the surgical table space, which can interfere with procedural operations in accessing equipment and tools, requiring more space or crowding the available space. The stand 10 reduces the amount of space on the table that is used for the bronchoscope 12 and its wires/tubes, making more space available for other equipment or tools.

Furthermore, laying the bronchoscope 12 on a table does not allow for routine warming of the tip of the Hopkins telescope. However, with the bronchoscope 12 on the stand 10, the warmer 14 is easily accessible. If the camera, which may be part of the Hopkins telescope, is allowed to come to room temperature while either the entire bronchoscope 12 or the Hopkins telescope is resting on the stand 10, the camera lens may fog when reinserted into the body of the patient, delaying use of the camera. Note that the Hopkins telescope, with its attached light cord and camera cord, may also be placed-while withdrawn from the bronchoscope 12—on the stand 10, and within the warmer 14, as it was while within the bronchoscope 12, providing additional benefit to users of the stand 10 while the bronchoscope 12 is being used without the Hopkins telescope.

Example users, without limitation, of the stand 10 include those practicing interventional pulmonology, which often involves bronchoscopes 12. However, bronchoscopy or endoscopy performed by thoracic and cardiothoracic physicians, as well as otolaryngologists, may also find benefit in using the stand 10 to support a variety of different endoscopes or bronchoscopes 12.

The detailed description and the drawings or figures are supportive and descriptive of the disclosure. While some of the best modes and other embodiments for carrying out the disclosure have been described in detail, various alternative designs, configurations, and embodiments exist for practicing the appended claims, as will be recognized by those having ordinary skill in the art.

The invention claimed is:

1. A stand usable for a bronchoscope, comprising:
   a base plate including an upper surface, a lower surface, a first edge connecting the upper surface to the lower surface, and a second edge connecting the upper surface to the lower surface, wherein the first edge is located on an opposite side of the base plate from the second edge;
   a first tower extending vertically from the upper surface of the base plate adjacent to the first edge of the base plate;

a second tower extending vertically from the upper surface of the base plate adjacent to the first edge of the base plate, wherein the first tower and the second tower are substantially parallel and each extends perpendicularly from the upper surface of the base plate;

a first receptacle groove at an opposite end of the first tower from the base plate;

a second receptacle groove at an opposite end of the second tower from the base plate; and a scope warmer attached to the upper surface of the base plate adjacent to the second edge, wherein a tip of the bronchoscope is configured to be received within the scope warmer.

2. The stand of claim 1, wherein:

the first receptacle groove is V-shaped, and the second receptacle groove is V-shaped.

3. The stand of claim 2, further comprising:

at least two cross bars extending between, and attached to, the first tower and the second tower.

4. The stand of claim 3, further comprising:

a third tower extending vertically from the upper surface of the base plate adjacent to the first edge of the base plate, wherein a proximal end of the third tower is in direct contact with the upper surface, a distal end of third tower intersects an uppermost of the at least two cross bars, and the third tower is located closer to the first edge than the first tower and the second tower.

5. The stand of claim 4, wherein:

the base plate is substantially square, and a height of the first tower and a height of the second tower are at least twice a width of the base plate, a height of the second tower from the base plate is greater than a height of the first tower from the base plate, and the height of the first tower and the height of the second tower is greater than a height of the third tower from the base.

6. The stand of claim 1, further comprising:

a third tower extending vertically from a proximal end at the upper surface of the base plate adjacent to the first edge of the base plate, such that the first tower, the second tower, and the third tower are clustered adjacent to the first edge and the third tower is located between the first tower and the third tower.

7. The stand of claim 6, wherein:

the base plate is substantially square, and a height of the first tower and a height the second tower are at least twice a width of the base plate, the height of the second tower from the base plate is greater than the height of the first tower from the base plate, and the height of the first tower and the height of the second tower are each greater than a height of the third tower.

8. The stand of claim 7, further comprising:

at least two cross bars extending between, and attached to, the first tower and the second tower, wherein a first end of each of the at least two cross bars is attached the first tower, a second end of each of the at least two cross bars is attached to the second tower, wherein a distal end of the third tower intersects an uppermost of the at least two cross bars.

9. The stand of claim 8, wherein the third tower includes a curve at a distal end and adjacent to the intersection with the uppermost of the at least two cross bars.

10. The stand of claim 1, wherein:

the first receptacle groove is V-shaped with a first branch and a second branch each extending from a distal end of the first tower, and the second receptacle groove is V-shaped with a first branch and a second branch each extending from a distal end of the second tower.

11. The stand of claim 10, further comprising:

three cross bars extending between, and attached to, the first tower and the second tower, wherein a first end of each of the three cross bars is attached the first tower, a second end of each of the three cross bars is attached to the second tower.

12. The stand of claim 11, further comprising:

a third tower extending vertically from the upper surface of the base plate adjacent to the first edge of the base plate, wherein a proximal end of the third tower is in direct contact with the upper surface and a distal end of third tower intersects an uppermost of the three cross bars and the third tower is located closer to the first edge than the first tower and the second tower.

13. The stand of claim 1, wherein:

the first receptacle groove includes a first branch and a second branch each extending from a distal end of the first tower, and the second receptacle groove a first branch and a second branch each extending from a distal end of the second tower.

14. A stand usable for a bronchoscope, comprising:

a base plate including an upper surface, a lower surface, a first edge connecting the upper surface to the lower surface, and a second edge connecting the upper surface to the lower surface, wherein the first edge is located on an opposite side of the base plate from the second edge, the base plate is substantially square, and the first edge and the second edge are separated from each other by side edges;

a first tower extending vertically from the upper surface of the base plate adjacent to the first edge of the base plate;

a second tower extending vertically from the upper surface of the base plate adjacent to the first edge of the base plate, wherein the first tower and the second tower are substantially parallel;

a first receptacle groove at an opposite end of the first tower from the base plate, wherein the first receptacle groove is substantially V-shaped;

a second receptacle groove at an opposite end of the second tower from the base plate, the second receptacle groove is substantially V-shaped; and a scope warmer attached to the upper surface on the base plate, wherein a tip of the bronchoscope is configured to be received within the scope warmer;

wherein a height of the first tower and a height of the second tower are at least twice a width of the base plate, the height of the second tower from the base plate is greater than the height of the first tower from the base plate.

15. The stand of claim 14, further comprising:

at least two cross bars extending between, and attached to, the first tower and the second tower, wherein a first end of each of the at least two cross bars is attached the first tower, a second end of each of the at least two cross bars is attached to the second tower.

16. The stand of claim 15, further comprising:

a third cross bar attached to the first tower and the second tower, wherein the third cross bar is an uppermost cross bar; and a third tower extending vertically from a proximal end adjacent to the first edge of the base plate;

wherein the third tower extends upward and curves to intersect the third cross bar with a distal end of the third tower and a height of the third tower is less than the height of the first tower and the height of the second tower.

17. The stand of claim 16, wherein:

a height of the third tower from the base plate is less than the height of the first tower and the height of the second tower.

18. The stand of claim 17, wherein:

The first tower and the second tower are each linear between a proximal end and a distal end and the third tower includes a curved portion adjacent a distal end.

19. A method for supporting a bronchoscope on a scope stand, comprising:

placing a tip of the bronchoscope in a scope warmer on a base plate of the scope stand, wherein the scope stand includes:

base plate having an upper surface, a lower surface, a first edge connecting the upper surface to the lower surface, and a second edge connecting the upper surface to the lower surface, wherein the first edge is located on an opposite side of the base plate from the second edge a first tower extending vertically from the upper surface of the base plate adjacent to the first edge of the base plate;

a second tower extending vertically from the upper surface of the base plate adjacent to the first edge of the base plate, wherein the first tower and the second tower are substantially parallel and each extends perpendicularly from the upper surface of the base plate;

a first receptacle groove at an opposite end of the first tower from the base plate;

a second receptacle groove at an opposite end of the second tower from the base plate; and the scope warmer is attached to the upper surface of the base plate adjacent to the second edge, wherein a tip of the bronchoscope is configured to be received within the scope warmer;

placing an upper portion of the bronchoscope into a first receptacle groove at a top of the first tower;

placing a tube extending from the bronchoscope into a second receptacle groove at a top of the second tower; and supporting the bronchoscope with the scope stand until used for a surgical procedure.

* * * * *